United States Patent [19]

Cirera et al.

[11] Patent Number: 4,835,179
[45] Date of Patent: May 30, 1989

[54] ANTIULCER DIHYDRODIBENZOCYCLOHEPTYLIDEN-ETHYLAMINE DERIVATIVES AND PROCESS FOR THE PREPARATION OF THESE COMPOUNDS

[75] Inventors: Xavier D. Cirera; Romeo R. Andreoli; Pedro P. Lloveras; Leonida Bruseghini; Jose P. Irurre, all of Barcelona, Spain

[73] Assignee: Sociedad Espanola de Especialidades Farmacotera peuticas, Barcelona, Spain

[21] Appl. No.: 54,409

[22] Filed: May 26, 1987

Related U.S. Application Data

[63] Continuation-in-part of Ser. No. 635,898, Jul. 30, 1984, abandoned.

[30] Foreign Application Priority Data

Aug. 2, 1983 [ES] Spain .................................. 524680

[51] Int. Cl.$^4$ ............................................. A61K 31/645
[52] U.S. Cl. ................................ 514/510; 514/656; 560/250; 564/363; 564/364
[58] Field of Search ............... 514/510, 656; 560/250; 564/363, 364

[56] References Cited

U.S. PATENT DOCUMENTS

| | | | |
|---|---|---|---|
| 3,906,110 | 9/1975 | Francis | 564/319 |
| 4,381,305 | 4/1983 | Casagrande | 514/357 |

FOREIGN PATENT DOCUMENTS

| | | |
|---|---|---|
| 2279389 | 2/1976 | France . |
| 49-43953 | 4/1974 | Japan . |
| 49-108053 | 10/1974 | Japan . |
| 52-105155 | 9/1977 | Japan . |
| 6507535 | 12/1966 | Netherlands . |
| 1128938 | 10/1968 | United Kingdom . |

OTHER PUBLICATIONS

Chemical Abstracts, 93:197538f, (1980).
Chemical Abstracts, 84:164397v, (1976).
Plilai, Agents Acting on the Central Nervous System: Part XXVI; Indian J. Chem., vol. 14B, Sep. 1976; pp. 714–716.
Chemical Abstracts, 81:120194k, (1974).

*Primary Examiner*—C. Warren Ivy
*Attorney, Agent, or Firm*—Michael J. Striker

[57] ABSTRACT

Dihydrodibenzocycloheptyliden-ethylene derivatives of the general formula:

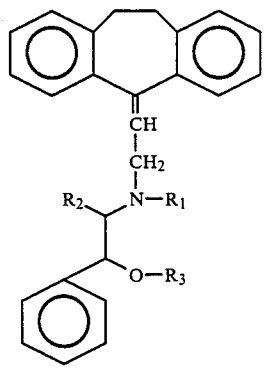

in which,
  $R_1$ represents an alkyl group having from 1 to 4 carbon atoms;
  $R_2$ represents a hydrogen atom or an alkyl group having from 1 to 4 carbon atoms; and
  $R_3$ represents a hydrogen atom, an alkyl group having from 1 to 4 carbon atoms or —CO—($C_1$-$C_4$ alkyl), are disclosed. These compounds are useful in the treatment of ulcer conditions.

3 Claims, No Drawings

ANTIULCER DIHYDRODIBENZOCYCLOHEPTYLIDEN-ETHYLAMINE DERIVATIVES AND PROCESS FOR THE PREPARATION OF THESE COMPOUNDS

CROSS-REFERENCE TO RELATED APPLICATION

This application is a continuation-in-part of application Ser. No. 635,898, filed July 30, 1984.

BACKGROUND OF THE INVENTION

The invention concerns pharmacologically active compounds derived from dihydrodibenzocycloheptylidenethylamine, useful in the treatment of pathologies responsive to antiulcer agents.

Many agents displaying such activity are known. For example, ranitidine and cimetidine are antiulcer agents. However, the activity of these agents is not always satisfactory.

It is therefore an object of the present invention to provide new pharmacologically active compounds displaying this activity.

SUMMARY OF THE INVENTION

This object is attained according to the present invention by novel compounds derived from dihydrodibenzocyclohepyliden-ethylamine of the general formula (I-A)

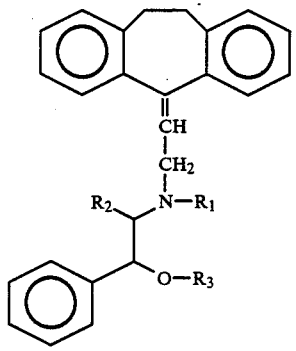

wherein, $R_1$ represents an alkyl group having from 1 to 4 carbon atoms;

$R_2$ represents a hydrogen atom or an alkyl group having from 1 to 4 carbon atoms; and, $R_3$ represents a hydrogen atom, an alkyl group having from 1 to 4 carbon atoms or —CO—($C_1$-$C_4$ alkyl).

Salts and other derivatives of the compounds of Formula I-A, likewise of pharmacological interest, such as N-oxides and quaternary ammonium salts are also included within the scope of the present invention, as well as the process for the production of said compounds and their derivatives, and therapeutic applications of the same.

The compounds according to the present invention possess a marked antiulcer activity, as will be set forth further below.

The compounds defined by the general formula I-A are prepared by reacting an amine of general formula II-A

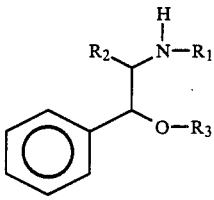

wherein $R_1$, $R_2$ and $R_3$ are the same as defined for general formula I-A, with a halogen derivative of the general formula III-A

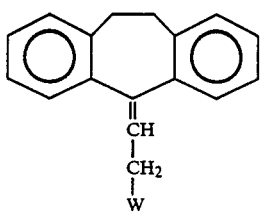

wherein, W is a chlorine or bromine atom.

The reaction is carried out in an inert solvent and in the presence of a hydrogen halide binder, which may be an inorganic or organic base, or an excess of the original amine. The compounds of general formula I-A may also be prepared by reacting the amines of general formula II-A with an aldehyde of formula IV,

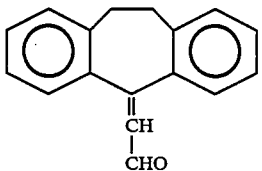

in the presence of a reducing agent, such as sodium borohydride or catalytic hydrogenation.

An alternative form for the compounds of formula I-A includes salts thereof with minimal acids, such as, for example, hydrochloric, sulfuric or nitric acid, or with organic acids, such as, for example, oxalic, salycylic, citric, maleic or fumaric acid. The employment of hydrochloric or maleic acid is, however, preferable, due to their favorable pharmacological properties.

In the embodiments which follow, the compounds of formula I-A are designated for purposes of simplicity by the alphabetic expression "WAS- . . . " followed by a number which is exclusive for the specific combination of substituent choices as set forth.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Examples 1 and 2 show chemical synthesis of the compounds according to the present invention:

EXAMPLE 1

Preparation of
(−)-N-2-(10,11-dihydrodibenzo-(a,d)cyclohept-5-yliden)-ethyl-ephedrine.

This compound is designated as WAS-4304.

A mixture of 5.10 g (20 mmoles) of 2-chloro-1-(10,11-dihydrodibenzo-(a,d)-cyclohept-5-yliden)-ethane and 6.60 g (40 mmoles) of (−)ephedrine base is refluxed in 100 ml of acetonitrile for 4 hours. After cooling, the solvent is eliminated and the residue taken up in chloroform and washed with 10% hydrochloric acid. The organic extract is dried over anhydrous sodium sulfate, after which the solvent is eliminated and the residue recrystallized from acetonitrile. 5.03 g of N-2-(10,11-dihydrodibenzo-(a,d)-cyclohept-5-yliden)-ethylephedrine are obtained in this manner.

Yield: 62%.

| Analytical data: | |
|---|---|
| Melting point: | 231–232° C. |
| IR: | 3370, 2020, 2510, 1600, 1485, 775, 760, 745, 705. |
| NMR: | 7.4/sc(13H); 6.4/t(1H); 6.0/t(1H); 5.5/sc(1H); 2.5–4.2/sc(8H). |
| $\alpha_D^{20} = 55.9$ | (C = 2; ethanol). |

EXAMPLE 2

Preparation of
(−)-N-2-(10,11-dihydrodibenzo-(a,d)-cyclohept-5-yliden)-ethyl-ephedrine. (WAS-4304).

A mixture of 2.34 (10 mmoles) of (10,11-dihydrodibenzo(a,d)cyclo-hept-5-ylidene)ethanal and 1.65 g (10 mmoles) of (−)-ephedrine is heated under reflux in 50 ml of methanol for ½-hour. After cooling, 0.38 g (10 mmoles) of sodium borohydride in methanol is added, during 15 min. The solvent is then removed, and the residue taken up in 50 ml of chloroform and washed with 10% hydrochloric acid. The organic phase is evaporated and the residue recrystallized from acetonitrile. 2.50 g of WAS-4304 hydrochloride are obtained in this way.

Yield: 61%.

The analytical data are the same as for Example 1.

In analogous manner the following examples set forth additional compounds according to the present invention. In each instance, the specific chemical structure and the analytical data for each of the compounds is shown, with the details of synthesis specified with reference to the aforementioned Examples 1 and 2.

The abbreviation IR in said Examples refers to the infrared spectrum, and the abbreviation NMR signified the proton nuclear magnetic resonance spectrum. The NMR analyses provide the following:

First, the position of the signal in parts per million (scale δ). The form or multiplicity of the signal is indicated by these next abbreviations:

s=singlet
d=doublet
t=triplet
q=quadruplet
sc=complex signal
sa=broad signal

The number of protons corresponding to each signal, obtained by electronic integration, is indicated between brackets.

In addition, some columns of Table 1 are headed by alphabetical signs, with the following significance:

Column A=No. of the Example
Column B=Brief denomination of the compound obtained and analyzed.
Column C=Indicates the number corresponding to the former Example (1 or 2) in which the method of preparation has been described in detail.
Column D=melting point in degrees C.
(*)=as maleate
(**)=as hydrochloride

TABLE 1

| | B | $R_1$ | $R_2$ | $R_3$ | C | Config. |
|---|---|---|---|---|---|---|
| Example 3 | WAS-4331 | $CH_3$ | $CH_3$ | H | 2 | 1S,2R |
| Example 4 | WAS-4329 | $CH_3$ | $CH_3$ | H | 2 | 1S,2S |
| Example 5 | WAS-4335 | $CH_3$ | $CH_3$ | H | 2 | 1R,2R |

| | D | $\alpha_D^{20}$ (C = 2EtOH) | NMR |
|---|---|---|---|
| Example 3 | 228–231 | +60.2 | 7.3/sc(13H); 6.3/t(1H) 6.0/t(1H); 5.4/sc(1H) 2.4–4.1/sc (8H) |
| Example 4 | 189–191 | −50.4 | 7.1/sc(13H); 6.5/t(1H) 6.2/t (1H); 5.3/sc(1H) 2.5–4.3/sc(8H) |
| Example 5 | 188–190 | +51.1 | 7.1/sc(13H); 6.5/t (1H) 6.2/t(1H); 5.3/sc(1H); 2.5–4.3/sc(8H) |

| | B | $R_1$ | $R_2$ | $R_4$ | $R_3$ | Config. | C |
|---|---|---|---|---|---|---|---|
| Example 6 | WAS-4389 | $CH_3$ | $CH_3$ | $C_6H_5$ | —CO—$CH_3$ | — | 4 |
| Example 7 | WAS-4390 | $CH_3$ | $CH_3$ | $C_6H_5$ | —CO—$C_2H_5$ | — | 4 |
| Example 8 | WAS-4391 | $CH_3$ | $CH_3$ | $C_6H_5$ | —$CH_3$ | — | 4 |

| | D | $\alpha_D^{20}$ (C = 2EtOH) | NMR |
|---|---|---|---|
| Example 6 | 203 — 204 (**) | — | 7.4/sc(13); 6.4/t(1); 6.0/t(1); 5.5/sc(1) 2.5–4.2/sc(8); 2.8/s(3); 2.1/s(3) 1.8/sc(3) |
| Example 7 | 197 — 198 (**) | — | 7.4/sc(13); 6.3/t(1); 5.9/t(1); 5.5/sc(1); 2.5–4.2/sc(10); 2.5/s(3); 1.9/sc(3); 1.7/t(3) |
| Example 8 | 189 — 190 (**) | — | 7.4/sc(13); 6.4/t(1); 6.0/t(1); 5.5/sc(1); 3.5/s(3)–2.5–4.2/sc(7); 2.8/s(3); 1.8/sc(3) |

PHARMACOLOGICAL PROPERTIES

The compounds according to the present invention possess antiulcer activity. What follows is a description of the methods used for evaluation of the above-mentioned pharmacological activity, together with the results obtained with the most representative compounds among those according to the present invention.

Antiulcer Activity

To evaluate this activity, the results of which are set out in the following Table 2. The technique employed is that of antagonism to indomethacine-induced ulcers in the rat according to the description of K. P. Bhargava, M. B. Crupta and K. K. Tangri (Eur. J. Pharm. 22, 191–195 (1973)). The $ED_{50}$ for antiulcer activity is calculated for the majority of the products which show greatest activity and the action of the remaining products is expressed using a system of crosses for comparison with the standard drug. The standard drugs used in this experiment are ranitidine and cimetidine.

The significance of the symbols is as follows:

++++ Very intense activity
+++ Considerable activity
++ Low activity
+ Low activity
0 Null activity

TABLE 2

| Compound | Compound Described in Example No. | Antiulcer Evaluation | Activity $ED_{50}$ mg/kg p.o. |
|---|---|---|---|
| WAS-4304 | 1 and 2 | ++++ | 0.069 |
| WAS-4331 | 3 | + | approx. 30 |
| WAS-4329 | 4 | 0 | >30 |
| WAS-4335 | 5 | 0 | >30 |
| WAS-4389 | 6 | +++ | 1.68 |
| WAS-4391 | 8 | +++ | 5.07 |
| WAS-4390 | 7 | no data | no data |

| Compound (standard drugs) | Compound Described in Example No. | Antiulcer Evaluation | Activity $ED_{50}$ mg/kg p.o. |
|---|---|---|---|
| Ranitidine | | ++++ | 8.2 |
| Cimetidine | | ++++ | 28.2 |

Toxicity

Table 3 sets forth the results of the indicative $LD_{50}$ for the most representative of the compounds according to the present invention.

The compounds are administered by the intraperitoneal route to Swiss mice, after which the toxic effects are observed, and the mortality rate and the $LD_{50}$ 7 days post-administration are calculated.

TABLE 3

| Compound | Compound Described in Example No. | Indicative $LD_{50}$ mg/kg i.p. |
|---|---|---|
| WAS-4304 | 1 and 2 | 115 |

Therapeutical Applications

The compounds described in the present invention have the following therapeutical applications:

Gastric and duodenal ulcer, Zollinder-Ellison syndrome, digestive hemorrhage due to lesions of the gastric mucosal layer; recurrent and post-anastomotic surgical ulcers; peptic oesophagitis.

PHARMACEUTICAL FORMS AND DOSAGE

All of the compounds according to the present invention can be administered by means of all the pharmaceutical forms compatible with their pharmacotechnical and therapeutic properties, at an adequate dosage. This includes tablets, dragees, pills, capsules, powders, lozenges, syrups and the like for oral administration, suppositories for rectal administration, and injection solutions for parenteral administration. The daily dose of the active pharmaceutical product may vary over a wide margin between 0.1 mg and 1,500 mg depending on the therapeutic application and the form of administration.

While the invention has been illustrated and described as embodied in dihydrodibenzocycloheptyliden-ethylamine derivatives and process for preparation thereof, it is not intended to be limited to the details shown, since various modifications and structural changes can be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

What is claimed is:

1. A dihydrodibenzocycloheptyliden-ethylamine derivative having the structural formula:

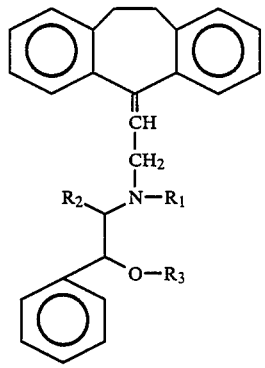

wherein, $R_1$ represents an alkyl group having from 1 to 4 carbon atoms;

$R_2$ Represents a substituent selected from the group consisting of a hydrogen atom and an alkyl group having from 1 to 4 carbon atoms; and $R_3$ represents a substituent selected from the group consisting of a hydrogen atom, an alkyl group having from 1 to 4 carbon atoms and —CO—($C_1$-$C_4$ alkyl).

2. A pharmaceutical composition for use in the treatment of ulcers having at least one compound according to claim 1, as an active ingredient, in combination with a suitable pharmaceutical carrier agent.

3. A process for the treatment of ulcers by administration of an effective amount of the pharmaceutical composition of claim 2.

* * * * *

UNITED STATES PATENT AND TRADEMARK OFFICE
CERTIFICATE OF CORRECTION

PATENT NO.    :   4,835,179

DATED         :   May 30, 1989

INVENTOR(S)   :   Xavier D. Cirera, Romeo R. Andreoli, Pedro P. Lloveras, Leonida Bruseghini, Jose P. Irurre It is certified that error appears in the above-identified patent and that said Letters Patent is hereby corrected as shown below:

On the title page:

In the heading [73], the name of the assignee should read:

-- Sociedad Espanola de Especialidades Farmaco-Terapeuticas, S.A. --

Signed and Sealed this

Seventeenth Day of July, 1990

Attest:

HARRY F. MANBECK, JR.

*Attesting Officer*   *Commissioner of Patents and Trademarks*